United States Patent [19]

Lewis

[11] 4,275,714

[45] Jun. 30, 1981

[54] SPINAL POSITIONING COUCH

[76] Inventor: Sidney E. Lewis, 89 Cherry Dr., Northcliff View, Johannesburg, Transvaal, South Africa

[21] Appl. No.: 49,652

[22] Filed: Jun. 18, 1979

[30] Foreign Application Priority Data

Jun. 23, 1978 [ZA] South Africa ........................ 78/3606

[51] Int. Cl.[3] ............................ A61F 5/00; A47C 1/12

[52] U.S. Cl. ........................................ 128/74; 128/70; 297/330; 297/460; 5/62; 5/432; 5/436

[58] Field of Search ..................... 128/33, 24 R, 25 R, 128/69, 70, 74; 5/62, 432, 436; 297/330, 71, 284, 460, 457; 269/323, 324, 328; 212/144, 134, 93

[56] References Cited

U.S. PATENT DOCUMENTS

| | | | |
|---|---|---|---|
| 1,904,039 | 4/1933 | Bruder | 128/69 |
| 2,715,901 | 8/1955 | Blake | 128/24 R |
| 2,987,116 | 6/1961 | Golden | 297/330 |
| 3,172,699 | 3/1965 | Naughton | 297/330 |
| 3,286,708 | 11/1966 | Gärtner | 128/70 |
| 3,361,471 | 1/1968 | Radford | 297/460 |
| 3,463,145 | 8/1969 | Whitaker | 128/24 R |
| 3,590,812 | 1/1969 | Larson | 128/33 |
| 3,794,023 | 2/1974 | Bradley | 128/24 R |
| 4,142,520 | 3/1979 | Herbuld | 128/74 |

FOREIGN PATENT DOCUMENTS

| | | | |
|---|---|---|---|
| 713376 | 7/1965 | Canada | 297/457 |
| 7605961 | 12/1976 | Netherlands | 128/70 |

*Primary Examiner*—Robert W. Michell
*Assistant Examiner*—Arthur S. Rose
*Attorney, Agent, or Firm*—Young & Thompson

[57] ABSTRACT

A chair intended for therapeutic use has integral seat, back and leg support zones mounted for rocking movement between limiting positions defined by the surface on which the chair stands. The back support zone is formed with a hump positioned to project the lumbar region of the user upwardly relatively to the rest of his spinal column. The back zone terminates in a head portion that is adapted to position the head of the user correspondingly to the pattern of his projected lumbar position. The distance from the seat zone center of the seat portion to the end of the head portion is approximately 900 mm and to the center of the lumbar support zone approximately 600 mm. The leg and back zones are inclined to each other at about 150°.

5 Claims, 2 Drawing Figures

SPINAL POSITIONING COUCH

FIELD OF THE INVENTION

This invention relates to a chair and particularly to a reclining chair which is adapted physiologically to revitalise a user by inducing a state of relaxation and postural correction.

SUMMARY OF THE INVENTION

A chair according to the invention includes a body support portion having integral seat, back and leg support zones which are arranged in a fixed relationship, with the leg support zone, from approximately the centre of the seat support zone, being inclined at a mean angle of between 130° and 170° relatively to the back support zone, and a frame on which the body support portion is mounted for movement between a first position in which the end of the leg support zone is adjacent a surface on which the frame rests and a second position in which the end of the back support zone is adjacent the surface.

In a preferred form of the invention the back support zone of the body portion of the chair includes an outwardly convex lumbar and upper thoracic region, which is so exaggerated that the portion of the spine, including the thoracic vertabrae T11, T12 and L1, of a person lying in the chair are moved forwardly relatively to the remainder of the person's spine.

Conveniently, the body support portion of the chair is pivotally connected to the frame and the chair includes means connected between the body support portion and the frame which is adapted for operation by means of a hand crank for moving the body support portion of the chair between its two positions of movement relatively to the frame. The chair may include means on the frame for holding the body portion of the chair in a selected position relatively to the frame between its two positions of movement.

A body support portion of a reclining chair according to the invention includes integral seat, back and leg support zones which are arranged in a fixed relationship, with the leg support zone, from approximately the centre of the seat support zone, inclined at an angle of approximately 150° relatively to the back support zone and an outwardly convex lumbar support region on the back support zone which is adapted to move the portion of the spine including thoracic vertabrae T11, T12 and L1 of a person lying on the body support portion of the chair forwardly relatively to the remainder of the person's spine.

BRIEF DESCRIPTION OF THE DRAWINGS

An embodiment of the invention is now described by way of example with reference to the drawing in which.

DETAILED DESCRIPTION OF THE PREFERRED EMBODIMENT

Figure 1:
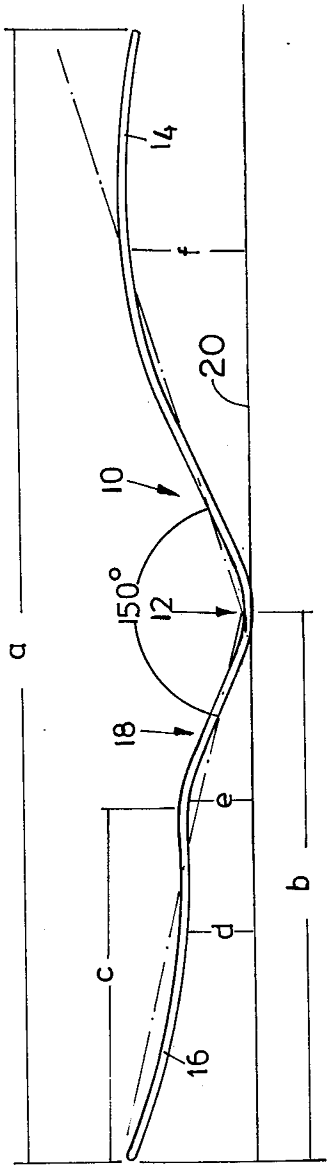
FIG. 1 is a side elevation of the body support portion of the chair resting on a flat surface.

The body support portion 10 of the chair of the invention is shown in FIG. 1 to include a seat zone indicated generally at 12, a leg support portion 14 and a back and head support portion 16. The back support portion of the body support includes an exaggerated outwardly convex lumbar support zone 18. The average or mean angle of inclination, indicated by the chain line, between the leg and back support portions of the chair is, when measured from the approximate centre of the seat zone 12 about 150°.

FIG. 1 is drawn approximately to scale and with the body support portion 10 of the chair laid on a flat surface 20 as illustrated in the drawing and with both ends of the support each 200 mm from the surface the approximate relative dimensions of the body support, and where relevant in relation to the surface, are:

a=1,900 mm
b=900 mm
c=600 mm
d=140 mm
e=110 mm
f=210 mm

The body support portion of the chair is, in this embodiment, made from a tubular frame which is transversely bridged by resilient plastic strip material, not shown, which is wound over and tensioned between the side members of the frame.

Figure 2:
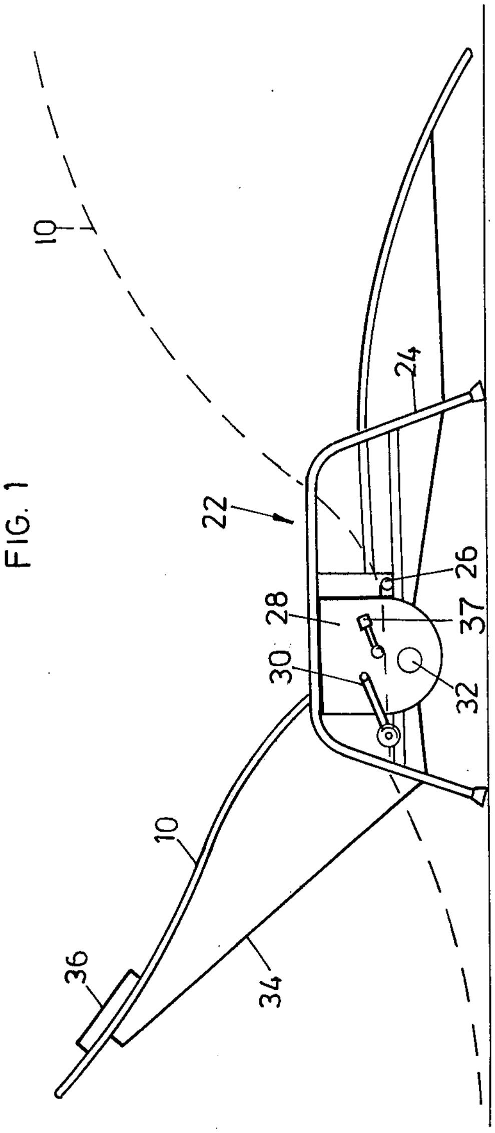
FIG. 2 is a side elevation of the chair.

The body support portion 10 of the chair is pivotally attached to a support member 22 as illustrated in FIG. 2.

The support member 22 consists of two spaced and inverted U-shaped side members 24 which are fixed relatively to each other by cross members which are not shown in the drawing.

The body support portion of the chair has a transverse crossbar fixed to the side members of its frame with the ends of the bar journalled for rotation in bushes 26 which are located in metal plates which extend vertically between the arm rest portion of the support members 24 and a crossbar.

A gear box 28 is fixed to one U-shaped member 24 and includes a crank handle 30, which through a reduction gear train in the box, is adapted to rotate a shaft 32 which extends horizontally under the body support to a bush in a plate on the opposite member 24. A cord 34 extends from a fastener on the underside of the head rest portion of the body support over a cross member between the rear most legs of the support 22, over a pulley which is fixed to the shaft 32 and over which the cord is wrapped, down over a cross member between the forward legs of the support 22 and to a fastener below the foot portion of the body support.

A slidable cushion 36 is positioned on the head rest portion of the back rest of the chair and is held in adjusted position by a flexible tape which is fastened to the outer crossbar of the body support portion 10 and which enables the cushion to move from the position shown in the drawing back towards the upper edge of the chair in use. The purpose of the adjustability of the cushion along the back rest is to accommodate different sizes of users, so to position the user that the cervical spine corresponds to the pattern of the re-alignment of the lumbar region imposed on him by the chair.

In use the chair may be moved, by an occupant, from the position shown in FIG. 2 to the position indicated in dotted lines and any intermediate position, by rotating the handle 30 which effectively shortens the bight of the cord 34 to the rear of the shaft 32 and increases its length between the pulley and its terminal on the foot rest.

The gear box 28 includes a catch 37 by means of which the body support portion of the chair may be locked in any selected position.

The invention is not limited to the precise constructional details as herein described and the body support portion of the chair could, for example, be directly coupled to the frame by a gear box so that the cord 34 may be eliminated. Additionally, in a slightly more elaborate version of the chair, the body support portion 10 could be made from a frame which is covered by upholstery. In other forms, the gear box could be disposed with and the chair locked in the desired orientation by a friction brake.

As mentioned in the introduction to this specification the chair of the invention is intended for therapeutic use in relaxation as opposed to merely an article of seating furniture and to this end the dimensions and contours of the body support portion 10 are extremely important as well as the fact that a user is able to obtain a degree of inversion by being able to rotate the body support portion 10 of the chair to the position illustrated by the dotted line in FIG. 2.

In the inverted or head-down position of the body support portion 10 of the chair, the user's buttocks are anchored in the seat support portion zone 12, and the hump of the lumbar support zone 18 prevents him from sliding on the chair in the fore-and-aft direction. His thoracic vertabrae, and particularly those denominated T11, T12 and L1 in anatomical parlance, are forwardly arched. The elevation of the legs and upward tilting of the pelvis causes a decompression of the lumbar region, or, otherwise put, a stretching of the spine in that region which increases the intervertabral spacing of the discs. This result is principally due to an elongation effect on the user's spine due to gravitational pull on his upper torso.

The effect of the stretching of the spinal column is dramatic. The tendency of the spinal discs to prolapse in the critical lower lumbar region, due to incorrect posture, is substantially reduced because the extension of the intervertabral spaces posteriorally decreases the centrifugal effect on the discs by exerting a counteracting centripetal force on them.

It is also very important that the head support region of the back rest be contoured and the adjustable cushion 36 so dimensioned and located that there is little or no forward or backward inclination of the user's head relatively to his spine while he is in the inverted position. The cervical spine is thus orientated to correspond to the pattern imposed by the chair on the lumbar region. The comments made above with regard to prolapsing of the spinal discs due to incorrect posture apply equally to the discs in the cervical zone.

The chair of the invention therefore provides three important features necessary for physiological revitalisation, namely, improved lung ventilation, increased head blood circulation and very importantly, relaxed spinal traction. The chair may even find important use in the treatment of certain spinal disorders and also help to prevent their occurrence.

I claim:

1. In a spinal positioning couch including a body support portion having head, back, seat and leg support zones and a support frame on which the body support portion of the couch is mounted for movement about a horizontal pivot connection between the body support portion and the frame; the improvement in which (a) the leg support zone from approximately the center of the seat support zone is inclined at a fixed mean angle of between 130° and 170° relatively to the back and head support zones;

(b) the back support zone includes an outwardly convex substantially non-deformable hump adapted to move the thoracic vertebrae T11, T12 and L1 of an adult user forwardly relatively to the remainder of his spinal column when the user lies on the couch in a supine position, (c) a head rest on the head support zone, and (d) means for moving the body support portion of the couch about its pivot connection with the frame between a substantially horizontal position and a position in which the head support zone is vertically lower than the seat support zone.

2. A couch as claimed in claim 1, in which the angle between the leg and back and head support zones is 150°.

3. A couch as claimed in claim 1, in which the apex of the hump on the back support zone is approximately 300 mm from the center of the seat support zone.

4. A couch as claimed in claim 1, in which the head rest is fixed to the head support zone of the couch by means which enables movement of the rest in the direction of a user's spine.

5. A couch as claimed in claim 1, in which with the body support portion of the couch held in a horizontal position with the free ends of the leg and head support portions of the support located 200 mm above a horizontal plane which contacts the lowest portion of the seat support zone the dimensions of the couch are approximately:

(a) total length 1,900 mm, (b) 900 mm between the center of the seat support and free end of the head support zones, (c) 600 mm between the free end of the head support zone and the apex of the hump on the back support zone, (d) at a point on the back support zone which is about 350 mm from the free end of the head support zone, 140 mm above the horizontal plane, (e) the apex of the hump on the back support zone, about 110 mm above the horizontal plane, and (f) at a point on the leg support zone about 600 mm from the center of the seat support zone, 210 mm above the horizontal plane.

* * * * *